United States Patent [19]

Schmitz et al.

[11] Patent Number: 5,134,381

[45] Date of Patent: * Jul. 28, 1992

[54] METHOD OF ANALYZING THE ALCOHOL CONTENT AND/OR THE CALORIFIC VALUE OF FUELS

[75] Inventors: Günter Schmitz; Bernd Reggelin, both of Aachen, Fed. Rep. of Germany

[73] Assignee: FEV Motorentechnik GmbH & Co., KG, Aachen, Fed. Rep. of Germany

[*] Notice: The portion of the term of this patent subsequent to Aug. 7, 2007 has been disclaimed.

[21] Appl. No.: 535,536

[22] Filed: Jun. 11, 1990

[30] Foreign Application Priority Data

Jul. 1, 1989 [DE] Fed. Rep. of Germany ....... 3921707

[51] Int. Cl.⁵ ............................................. G01N 27/22
[52] U.S. Cl. .................... 324/685; 324/663; 73/61.41
[58] Field of Search ............... 324/650, 659, 663, 673, 324/674, 679, 680, 698, 685, 725, 690; 73/61.1 R

[56] References Cited

U.S. PATENT DOCUMENTS

| | | | |
|---|---|---|---|
| 3,324,049 | 5/1967 | Hanken | 324/674 |
| 4,112,744 | 9/1978 | Tassano | 324/679 |
| 4,288,741 | 9/1981 | Dechene et al. | 324/650 |
| 4,470,300 | 9/1984 | Kobayashi | 73/61.1 R |
| 4,801,863 | 1/1989 | Schimion et al. | 324/670 |
| 4,885,529 | 12/1989 | Lee et al. | 324/663 |
| 4,905,655 | 3/1990 | Maekawa | 73/861.08 |
| 4,907,442 | 3/1990 | Jones et al. | 324/663 |
| 4,939,468 | 7/1990 | Takeuchi | 324/686 |
| 4,945,863 | 8/1990 | Schmitz et al. | 723/1 A |

OTHER PUBLICATIONS

Proceedings of the Fourth International Symposium on Alcohol Fuels Technology, Sao Paulo, Brazil, Oct. 10, 1980, pp. 379-83.

Primary Examiner—Kenneth A. Wieder
Assistant Examiner—Maura K. Regan
Attorney, Agent, or Firm—Watson, Cole, Grindle & Watson

[57] ABSTRACT

A method of determining the alcohol content and/or the calorific vaue of fuels by containing the fuel and measuring the electrically measurable values in a measurement cell to determine the relative permittivity of the mixture as the characteristic of the alcohol content of the calorific value. The relative permittivity is then determined by means of a computer or circuitry, independent of the influence of the conductivity of the fuel.

22 Claims, 3 Drawing Sheets

METHOD OF ANALYZING THE ALCOHOL CONTENT AND/OR THE CALORIFIC VALUE OF FUELS

RELATED APPLICATIONS

The present application relates to commonly owned U.S. Pat. applications Ser. No. 391,248, filed Aug. 9, 1989 and Ser. No. 329,839, filed Mar. 23, 1989U.S. Pat. No. 4,945,865; Ser. No. 446,781, filed Dec. 6, 1989; Ser. No. 446,726, filed Dec. 8, 1989; Ser. No. 446,780, filed Dec. 6, 1989; Ser. No. 446,728, filed Dec. 6, 1989; and concurrently filed application Attorney Docket No. 64172, Ser. No. 535,062, filed June 8, 1990, relating to West German Application No. P 39 22 851.7 filed July 12, 1989, which are hereby incorporated by reference.

BACKGROUND OF THE INVENTION

1. Technical Field of the Invention

The invention relates to a method of analyzing the alcohol content and/or the calorific value of fuels by measuring the electrically measurable values in a measurement cell containing the fuel, to determine the relative permittivity of the mixture as a characteristic of the alcohol content or the calorific value.

2. Discussion of the Related Art

In light of diminishing fossil energy reserves of fuels obtained from crude oil and stricter environmental protection requirements, increasing amounts of methyl or ethyl alcohol are being added to these fuels. Thus, any arbitrary refueling should be possible both with pure fuels and mixed fuels. When the alcohol content is higher, it is necessary to know the blending ratio in order to obtain optimal performance from the fuel-burning engine and to enable a precise proportioning of fuel adjusted to the operating conditions. The continuous determination of the alcohol content in the fuel fed into the fuel-burning engine in operation presents special problems for automobile engines in which any possible blend may be present by arbitrary refueling with various types of fuel.

The known optical processes are hardly suitable for this purpose since they often utilize interface effects to determine the refraction index, from which the alcohol content can be inferred. In addition to the difficulty of using these processes in automobile engines, another drawback of this process is that the mix to be observed must have a high homogeneity, especially at the interface. The required precision has not been achieved with this process.

Therefore, it has been proposed that the alcohol content in fuels be determined by means of a dielectric analysis. Such a process would solve the problem concerning measurement of the interface effects since measurement is done volumetrically. On the other hand, the conductance of the mixture significantly affects the volumetric dielectric analysis (cross sensitivity). Since the conductance is a function primarily of the pollutants or the water content, such a measuring process leads to useless results.

The possibility of determining the alcohol content of fuels by means of dielectric measurements is explored in the document "Proceedings of the Fourth International Symposium on Alcohol Fuels Technology," Sao Paulo, Brazil of Oct. 5, 1980. However, the process was rejected since the influences of temperature and conductance (induced by water content or other pollutants in the fuel) prevented a reliable measurement suitable for fuel-burning engines from being obtained.

Therefore, it is an object of the present invention to provide a process of the aforementioned kind which permits a precise and reliable determination of the alcohol content and/or calorific value in fuels, in particular for application in automobile engines.

Other objects and advantages will become apparent from the specification and drawings which follow.

SUMMARY OF THE INVENTION

The foregoing and additional objects are achieved by the present invention which determines the relative permittivity by measuring the capacitance of a capacitor formed in the measurement cell and whose dielectric is formed by means of the fuel contained in the measurement cell. The capacitance is then determined by means of a computer or circuitry, independent of the influence of the conductivity of the fuel.

A further embodiment provides that either an alternating voltage or a direct voltage, superimposed by alternating voltage, is applied to two capacitor electrodes in the measurement cell and the relative permittivity is determined as a function of the real and/or imaginary part of the characteristics of the flowing currents.

In an advantageous manner, the capacitance can be measured by loading the measurement cell with a sinusoidal voltage and by evaluating the current flowing through the measurement cell in light of the imaginary part. This can occur by means of a simple synchronous rectification or also by means of multiplication with a cosine-shaped voltage of equal frequency. The resulting output signal is then proportional to the capacitance.

DETAILED DESCRIPTION OF THE PREFERRED EMBODIMENTS

Figure 1:
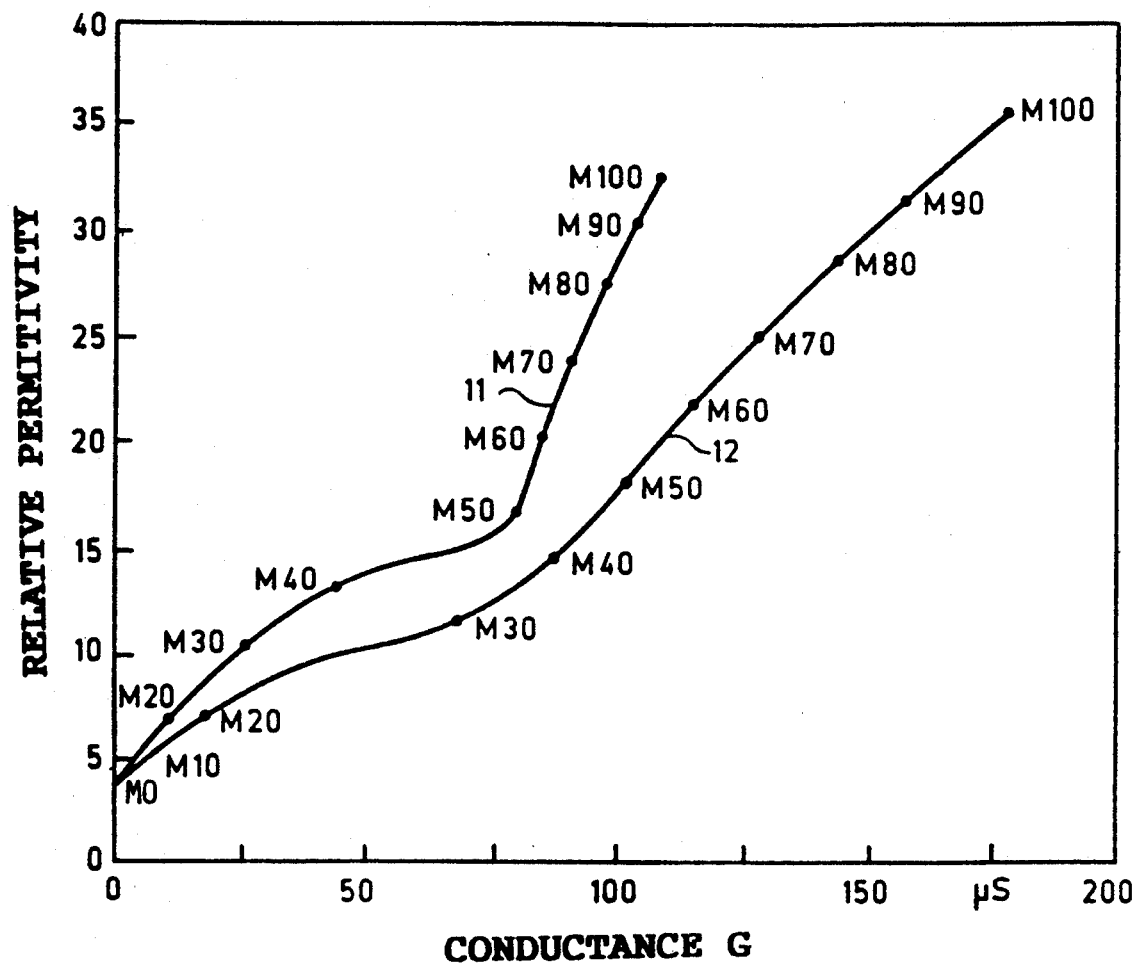
FIG. 1 a diagram of the relative permittivity as a function of the conductance G as a function of the water content and the methanol content of the fuel.

The present invention will now be described in greater detail with reference to the accompanying drawings. Referring to FIG. 1, the values of the dielectric measurement are plotted on the ordinate and the conductance G on the abscissa. Curve 11 shows the values of the dielectric measurement as a function of the proportion of methanol admixture with 0% water content in the fuel, whereas line 12 plots the corresponding values with 2.5% $H_2O$ content. The measured points for the variable percentages of methanol, ranging from 0% to 100% (MO to M100), are plotted on the curves.

When measuring the capacitance to determine the relative permittivity, problems arise due to the influence of the different conductivities.

It is apparent from FIG. 1 that a specific water content influences the conductance. Stronger influences on the conductance are also observed with acids and salts, which in even small concentrations can drastically increase the conductance without causing any significant change in capacitance. However, in oscillating circuits to determine the capacitance, different conductances have a negative effect. In RC circuits the result is a false measurement of the capacitance, which must be subsequently compensated for by measuring the conductance separately Finally, in LC circuits there is a problem with respect to the measurement error so severe that the basic ability of the circuit to oscillate is affected.

Once the capacitance and then the alcohol content is determined, the air ratio of the fuel in a fuel injection engine may be adjusted by known labda control.

It is possible to accurately determine the alcohol content by means of a capacitance determination—provided with a temperature-dependent correction—by means of measuring circuits which enable a suppression of the conductance influence through the analysis of mathematical correlations with a computer or appropriate circuitry.

Figure 2:
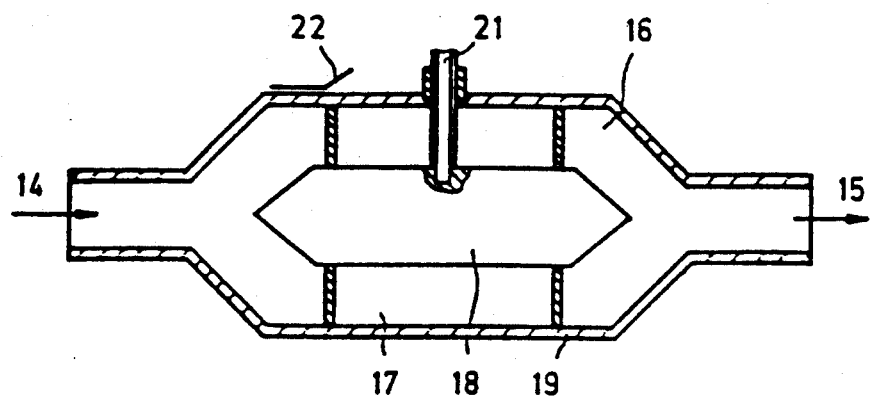
FIG. 2 shows an example of a measurement cell to carry out the process of the invention.

FIG. 2 shows an embodiment of a measuring cell 13 for carrying out the process of the invention. The fuel enters the measuring cell thorough in-flow 14 and exits the measuring cell through out-flow 15. In the areal presentation of FIG. 2, the current divides into current paths 16 and 17 which are formed by a center cylinder 18. The center cylinder 18 and the outer shell 19 conduct electricity partially or completely and thus these walls or parts of the walls of the measuring cell represent the electrodes of the capacitor of a measuring or evaluating circuit. Thus, the at least partially conductive wall of the measuring cell represents the first electrode and the at least partially conductive center cylinder or flow body 18 is the second electrode.

The center cylinder 18 and the outer shell 19 form the actual measuring capacitor which encloses the measured volume. The corresponding values can be scanned at the connectors 21 and 22.

Figure 3:
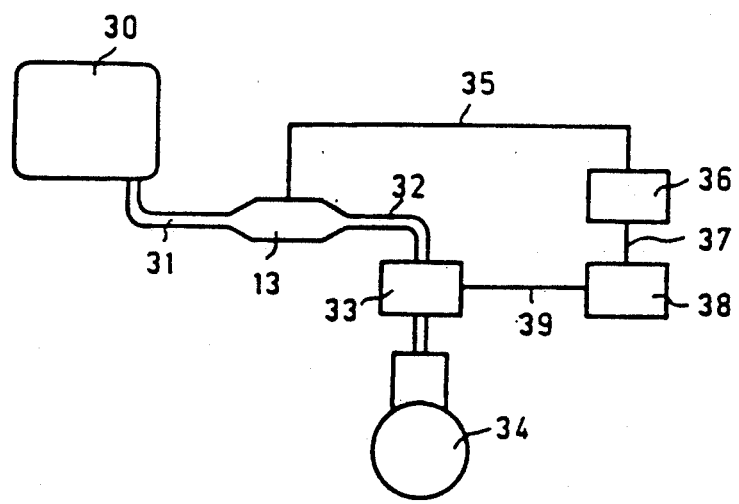
FIG. 3 is a schematic of a system to apply the process of the invention to control or adjust an injection fuel-burning engine.

As apparent from the schematic in FIG. 3, fuel mixed with alcohol flows from fuel tank 30 by means of a line 31 to the measurement cell 13 and from there by means of line 32 to a proportioning device 33, which, as a rule, is an injection pump with corresponding injection nozzles. The fuel is subsequently fed into the engine 34 by means of direct or indirect injection.

The values of the capacitance and conductance, scanned in the measuring cell 13, are fed by means of the measuring line 35 of a shared evaluation circuit or evaluation unit 36. It is especially advantageous if the alternating voltage is applied to the two capacitor electrodes in the measurement cell and the relative permittivity is determined as a function of the real and/or imaginary part of the characteristics of the flowing current.

The signals sent by the evaluation circuit 36 travel over a line 37 to an injection computer 38 and controls the proportioning device 33 via a line 39.

Thus, the mixing ratio evaluated in the evaluation unit 36 and measured in the measuring cell 13 is not operationally changed but rather the type of injection is changed depending on the measured and evaluated values. For example, when injection fuel-burning engines are controlled or adjusted, the measurement of the alcohol content of the supplied fuel serves to pre-control the injected quantity, whereas the air ratio is precision controlled by means of a known lambda control. When applying the process of the invention to injection fuel-burning engines, especially automotive engines, it may be suitable to integrate the shared circuit as the evaluation unit into the injection system by means of circuit and program technology. Other advantages can be attained with the process when the temperature of the fuel located in the measurement cell 13 is determined and fed into the evaluation unit to compensate for the influence of temperature.

Figure 4:
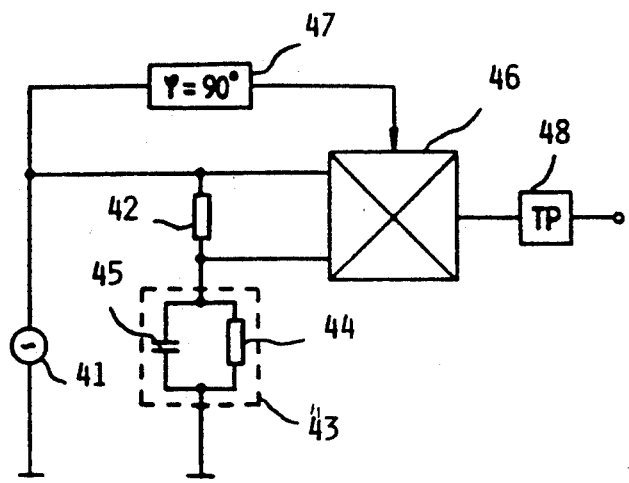
FIG. 4 shows an embodiment of a circuit to determine the relative permittivity by means of capacitance measurement.

FIG. 4 shows a preferred embodiment of a circuit to determine the capacitance. An alternating voltage source 41 loads a measurement cell 43 with a sinusoidal voltage by means of a resistance resistor 42 which operates as a current sensor. The resulting current flow, which is scanned at the resistor 42 as the drop in voltage, contains a real part which depends only on the conductance 44 of the measurement cell and an imaginary part which depends only on the capacitance 45 of the measurement cell. To evaluate the imaginary part exclusively, the scanned current is multiplied with a cosinusoidal voltage in a multiplier 46, which is obtained, e.g. from the sinusoidal voltage via a phase shifter 47. The direct voltage share of the multiplicator output voltage, which represents a measure for the capacitance, is extracted by means of a low pass filter 48. Instead of a multiplication, a simple synchronous rectification can also be performed.

Figure 5:
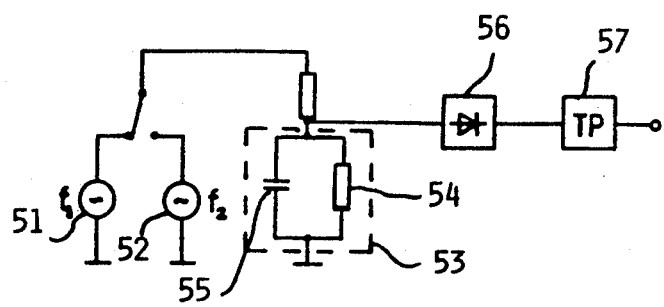
FIG. 5 shows an embodiment of a circuit in which the measurement is conducted with the said of different frequencies.

According to FIG. 5, another advantageous embodiment is obtained if two different frequencies of two voltage generators 51 and 52 are used with conductance 54 and capacitance 55 to measure the drop in voltage at the measurement cell 53. Then only the amount of the output voltage, formed by means of a rectifier 56 and a low pass filter 57, is evaluated.

Alternatively, the capacitance of the measurement cell can be used as the frequency-determining member of an oscillating circuit, wherein the capacitance causes a cross influence.

Figure 6:
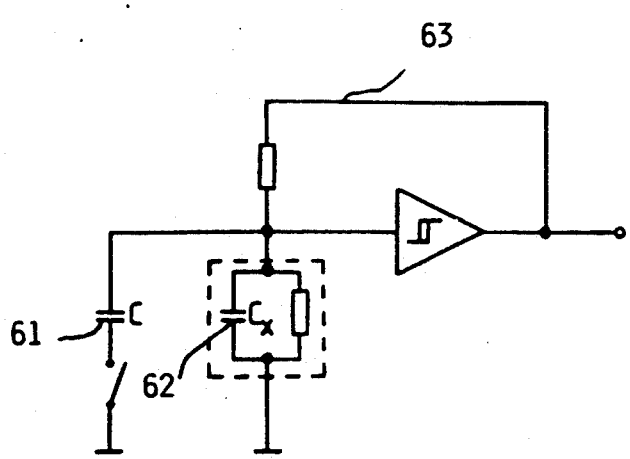
FIG. 6 shows another embodiment in which the measurement is conducted in two phases.

According to FIG. 6, the measurement is performed in two phases. During the second measurement, a defined capacitance C of the capacitor 61 is switched parallel to the measurement cell capacitance Cx of the measurement cell 62. Thus, two different frequencies are obtained whose evaluation yields a statement about the capacitance. In the simplest case, the resulting formula is $$f2/f1 = Cx/(Cx+C),$$

where f1 is the frequency generated by the measurement cell 62 and f2 is the frequency generated by the parallel connection of the measurement cell 62 and the known capacitor 61. Preferably, f1 is held constant while the capacitor Cx varies. The frequency f1 may be adjusted by a switched capacitor circuit.

In light of mass production there are special advantages if, instead of the switched capacitance, a switchable delay is inserted, for example, into the feedback path 63. Like the parallel circuit of the capacitance, this delay lowers the frequency so that the frequencies can be evaluated in the same manner.

Another advantageous embodiment consists of conducting the measurement with the said of a measuring bridge. In this process the bridge should be self-balancing so that the value adjusted for the capacitance is evaluated as the measure for the capacitance of the measurement cell.

Since the correlation between relative permittivity and alcohol content depends heavily on the temperature, it is expedient to link the capacitive measured value with the value of the fuel temperature in order to obtain an output quantity that is independent of the temperature as the measure for the alcohol content. This linking can be performed together with a linearization of the output voltage with the said of a processor. Especially preferred is the application of the processor normally used for the injection or ignition.

For another application in the field of internal combustion engines, it is also advantageous if the measured quantities and the linearization are linked in the sensor, and in particular without a processor by means of a circuit that is as simple and cost-effective as possible. To this end, the values for the temperature and the capacitance are guided as the digital values on the address lines of a programmable component, e.g., a ROM, EPROM or PAL. Then the information about the alcohol content is scanned in digital format at the data lines of the corresponding programmed EPROM, among others, and is fed, if desired, to a D/A converter for conversion into an analog value. One of the output lines can also be used to give error signals which can determine out-of-range signals and thus malfunctions of the sensors.

Another embodiment is obtained by using a frequency or a frequency range in which, due to the failure of specific polarization mechanisms, the excessive relative permittivity just before the failure frequency is used for the measurement point of view.

Other improvements and modifications will become apparent to one skilled in the art without departing from the spirit and scope of the present invention as defined by the following claims.

We claim:

1. A method for analyzing a fuel which may contain alcohol in solution, comprising the steps of:
   containing the fuel in a measurement cell;
   applying an alternating voltage or current, respectively, to two electrodes forming a capacitor arranged in the measuring cell, the electrodes having the fuel as a dielectric there between;
   determining the capacitance independently of fuel conductivity as a function of real and/or imaginary characteristics of the resulting current flow or voltage, respectively of the capacitor; and
   determining an alcohol content of the fuel from the determined capacitance.

2. The method according to claim 1, wherein said measuring step further comprises loading the electrodes with a sinusoidal voltage and evaluating the imaginary part of the current.

3. The method according o claim 1, wherein said determining step further comprises switching a defined capacitance C parallel the capacitance determined by the measuring cell.

4. The method according to claim 1, further comprising measuring the temperature o the fuel within the measuring cell and using this temperature to correct the value o the determined alcohol content.

5. The method according o claim 2, wherein the imaginary part of the current is evaluated by synchronous rectification.

6. The method according to claim 2, wherein the imaginary part of the current is evaluated by multiplying the current signal with a cosine-shaped signal.

7. The method according to claim 1, wherein one of the two electrodes is a wall of the measurement cell.

8. A method of analyzing a fuel, comprising the steps of:
   containing the fuel in a measurement cell;
   measuring the capacitance o a capacitor formed in the measurement and having the fuel as its dielectric, said measuring step being accomplished independently of any influence of fuel conductivity; and
   determining an alcohol content of the fuel from the measured capacitance.

9. The method according to claim 8, wherein a frequency measured by the capacitor is held constant while the capacitance o the fuel varies.

10. The method according to claim 9, wherein the frequency is adjusted by a switched capacitor circuit.

11. The method according to claim 8, wherein said determining step comprises loading the electrodes with two voltages of different frequency and evaluating the respective resulting voltage drop across the electrodes or the respective current flow through the capacitor.

12. The method according to claim 8, wherein determining step further comprises switching a defined capacitance parallel to the capacitance determined by the measuring cell, and obtaining the capacitance Cx of the fuel by the following relationship:

$$f2/f1 = Cx/(Cx+C),$$

where f1 and f2 re respective frequencies determined by the capacitor and determined capacitance, wherein t least one of the frequencies lies in the rang of excessive relative permittivity of the fuel.

13. The method according to claim 12, wherein said switching is accomplished via a switchable delay member.

14. The method according to claim 14, wherein said determining of the capacitance is performed by a self-balancing measuring bridge.

15. The method according to claim 8, wherein the capacitance and temperature of the fuel are evaluated directly in a ROM without application of a processor, resulting digitalized values are used as an address, and the alcohol content is determined from the state of associated digital lines.

16. The method according to claim 12, wherein said determining step further comprises switching a switchable delay member in feedback relation with the measuring cell.

17. The method according to claim 8, further comprising measuring the temperature of the fuel within the measuring cell and using this temperature to correct the value of the determined alcohol content.

18. The method according to claim 11, further comprising measuring the temperature of the fuel within the measuring cell nd using this temperature to correct the value o the determined alcohol content.

19. The method according to claim 12, further comprising measuring the temperature of the fuel within the measuring cell and using this temperature to correct the value of the determined alcohol content.

20. The method according to claim 14, further comprising measuring the temperature of the fuel within the measuring cell and using this temperature to correct the value of the determined alcohol content.

21. The method according to claim 15, further comprising measuring the temperature of the fuel within the measuring cell and using this temperature to correct the value of the determined alcohol content.

22. The method according to claim 16, further comprising measuring the temperature of the fuel within the measuring cell and using this temperature to correct the value of the determined alcohol content.

* * * * *